United States Patent
Tritthart

(10) Patent No.: US 10,772,996 B2
(45) Date of Patent: Sep. 15, 2020

(54) DEXAMETHASONE COATING FOR USE WITH ELECTRODE CARRIER

(71) Applicant: MED-EL Elektromedizinische Geraete GmbH, Innsbruck (AT)

(72) Inventor: Thomas Tritthart, Völs (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 0 days.

(21) Appl. No.: 16/484,907

(22) PCT Filed: Feb. 7, 2018

(86) PCT No.: PCT/US2018/017154
§ 371 (c)(1),
(2) Date: Aug. 9, 2019

(87) PCT Pub. No.: WO2018/148232
PCT Pub. Date: Aug. 16, 2018

(65) Prior Publication Data
US 2019/0381219 A1  Dec. 19, 2019

Related U.S. Application Data

(60) Provisional application No. 62/456,726, filed on Feb. 9, 2017.

(51) Int. Cl.
*A61L 31/16* (2006.01)
*B05D 1/02* (2006.01)
(Continued)

(52) U.S. Cl.
CPC ............ *A61L 31/16* (2013.01); *A61K 31/573* (2013.01); *A61L 31/10* (2013.01); *B05D 1/02* (2013.01);
(Continued)

(58) Field of Classification Search
CPC .............................. A61L 31/16; B05D 3/0254
(Continued)

(56) References Cited

U.S. PATENT DOCUMENTS 7,658,727 B1 * 2/2010 Fernandes ............. A61F 2/2403
604/265
8,372,646 B1 * 2/2013 Chattaraj ............... G01N 30/68
436/161

(Continued)

FOREIGN PATENT DOCUMENTS

| EP | 0923953 A2 | 6/1999 |
| EP | 0923953 A3 | 11/2000 |
| WO | 00/57948 A1 | 10/2000 |

OTHER PUBLICATIONS

Ghavi et al. Corticosteroid-releasing cochlear implant: A novel hybrid of biomaterial and drug delivery system. Journal of Miomedical Materials Research B: Applied Biomaterials. vol. 94B, Issue 2. Aug. 2010 (Year: 2010).*

European Patent Office, International Search Report and the Written Opinion of the International Searching Authority, Application No. PCT/US2018/017154, dated May 18, 2018, 12 pages.

*Primary Examiner* — Cachet I Proctor
(74) *Attorney, Agent, or Firm* — Sunstein LLP

(57) ABSTRACT

A method of forming a silicone coating on an electrode carrier for use in cochlear implant systems includes dissolving silicone and dexamethasone in a solvent to form a solution, adding a non-solvent to the solvent, the non-solvent miscible with the silicone and the dexamethasone having a solubility in the non-solvent of below about 5 mg/ml, and curing the solution to form the silicone coating on the electrode carrier.

21 Claims, 5 Drawing Sheets

(51) Int. Cl.
*A61K 31/573* (2006.01)
*A61L 31/10* (2006.01)
*B05D 3/02* (2006.01)
*B05D 3/14* (2006.01)
*B05D 7/24* (2006.01)
*A61N 1/05* (2006.01)

(52) U.S. Cl.
CPC ........... *B05D 3/0254* (2013.01); *B05D 3/142* (2013.01); *B05D 7/24* (2013.01); *A61L 2300/222* (2013.01); *A61L 2300/41* (2013.01); *A61L 2420/02* (2013.01); *A61L 2420/06* (2013.01); *A61N 1/0541* (2013.01)

(58) Field of Classification Search
USPC ....................................................... 427/2.24
See application file for complete search history.

(56) References Cited

U.S. PATENT DOCUMENTS

| | | | | |
|---|---|---|---|---|
| 2009/0062896 | A1* | 3/2009 | Overstreet | A61N 1/0541 607/137 |
| 2009/0292237 | A1* | 11/2009 | Overstreet | A61K 9/0046 604/20 |
| 2011/0071596 | A1* | 3/2011 | Kara | B82Y 30/00 607/57 |
| 2012/0141572 | A1* | 6/2012 | Hessler | A61L 27/34 424/422 |
| 2013/0079749 | A1* | 3/2013 | Overstreet | A61M 31/00 604/514 |
| 2014/0364793 | A1* | 12/2014 | D'Hiver | A61L 31/16 604/20 |

* cited by examiner

DEXAMETHASONE COATING FOR USE WITH ELECTRODE CARRIER

CROSS-REFERENCE TO RELATED APPLICATIONS

This application is the national phase entry of International Patent Application No. PCT/US2018/017154 filed Feb. 7, 2018, which claims the benefit of U.S. Provisional Patent Application No. 62/456,726 filed Feb. 9, 2017, the disclosures of which are incorporated by reference herein in their entirety.

The present application claims the benefit of U.S. Provisional Patent Application No. 62/456,726 filed Feb. 9, 2017, the disclosure of which is incorporated by reference herein in its entirety.

TECHNICAL FIELD

The present invention relates to a method of forming a coating on an electrode carrier, and more specifically to a method of forming a silicone coating containing dexamethasone on an electrode carrier for a cochlear implant system.

BACKGROUND ART

Implantable auditory prostheses have been developed, such as cochlear implant systems, to improve impaired hearing in patients. In implantable systems, it is important to minimize the physical trauma caused by the insertion and placement of the stimulation electrode in order to reduce the risk of further hearing loss due to the insertion process itself. The use of a drug, during and/or after implantation, may help to minimize the trauma, and the stimulation electrode may be used to deliver the drug locally. For example, the stimulation electrode may be formed from a silicone material embedded with the drug or the silicone material may have a coating embedded with the drug so that the drug is released over time to the surrounding tissue. In some cases, however, it is difficult or not possible to form a thin, uniform coating with the drug that allows the release of the drug from the coating in a desired way.

U.S. Pat. No. 7,022,372 describes a method for coating an implantable device by dissolving a poly(ethylene-co-vinyl) alcohol and a drug in a solvent comprising a first solvent and a co-solvent with a low dielectric constant to form a solution. The co-solvent includes unsubstituted or substituted aliphatic hydrocarbons including n-hexane, n-pentane or cyclohexane. The patent discloses use of dimethylacetamide (DMAC) or dimethylsulfoxide (DMSO) to dissolve the polymer. The properties of the solvents (high surface energy, viscosity and degree of wetting of the substrate) can lead to less than optimal coating, and the patent discloses that the quality of the coating can be improved by adding a co-solvent. The improvement of the coating quality, when a co-solvent is added, is shown as having a low viscosity, low surface energy or low dielectric constant for the poly(ethylene-co-vinyl) alcohol. The patent discloses that the coating quality can also be improved, if a co-solvent is added having a low surface energy.

U.S. Pat. No. 5,562,922 describes that a drug can be incorporated into polyurethane by a mixture of solvent which swells (expands) but does not dissolve the polymer. An added drug can be incorporated in the interstices of the polymer. However, a swelling process would probably need long process times and a cleaning of the contact plates and areas where the drug should not be present.

U.S. Patent Appl. No. 2011/0229627 describes a method for electrospray coating of objects. The method creates electrically charged particles which then form a coating when applied to a specific substrate. The coating is prepared by sending liquid droplets containing a biologically active ingredient, a polymer dispersed in a solvent or mixture therefrom.

U.S. Pat. No. 8,030,326 discloses crystalline forms of rapamycin analogs as well as compositions, uses, and methods for aking the sa rye. A crystalline form of rapamycin is prepared, including a solvate, for instance THF, incorporated into the crystal structure. The patent describes various crystallization processes.

U.S. Patent Appl. No. 2009/0197850 describes a coating containing a drug in a polymer. The release can be controlled by the degree of crystallinity of the polymer.

WO2002/058753 discloses a method of forming a coating for an implantable device that includes forming a primer and a reservoir region. The primer region is usually used for improving the adhesion of the drug containing polymer to the implant.

U.S. Pat. No. 8,383,142 describes the use of different solvent mixtures to improve the wettability of the coating solution to the substrate usually a metal of a stent.

FIG. 1 schematically shows some components of a typical cochlear implant system in a human ear. The cochlear implant system includes an external microphone which provides an audio signal input to an external signal processor 111 which implements one of various known signal processing schemes. The processed signal is converted by the external signal processor 111 into a digital data format, such as a sequence of data frames, for transmission by an external coil 107 into a receiving stimulator processor 108. Besides extracting the audio information, the receiving stimulator processor 108 may perform additional signal processing, such as error correction, pulse formation, etc., and produces a stimulation pattern (based on the extracted audio information) that is sent through to an implanted stimulation electrode. The stimulation electrode is typically made of a flexible silicone electrode carrier with wires embedded within the silicone that are connected to stimulation contacts on the surface of the carrier. The stimulation electrode includes an electrode lead 109 and an electrode array 110, which is gently inserted into the scala tympani of the cochlea 104. Typically, the electrode array 110 includes multiple stimulation contacts 112 distributed along its surface that provide selective electrical stimulation of the cochlea 104. The electrode contacts may also be used for sensing neural tissue response signals, e.g., the stimulation electrode may also function as a measurement electrode.

Other parts of the ear are also shown in FIG. 1. The ear usually transmits sounds, such as speech sounds, through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. The cochlea 104 forms an upright spiraling cone with a center called the modiolus where the axons of the auditory nerve 113 reside. In response to received sounds transmitted by the middle ear 103, the fluid-filled cochlea 104 functions as a transducer to convert mechanical motion and energy and, in response, to generate electric pulses which are transmitted to the auditory nerve 113, and ultimately to the brain. As mentioned above, in patients with a cochlear implant system, the implanted electrode array 110 provides the electrical stimulation to the cochlea 104.

SUMMARY OF EMBODIMENTS

In accordance with one embodiment of the invention, a method of forming a silicone coating on an electrode carrier for use in cochlear implant systems includes dissolving silicone and dexamethasone in a solvent to form a solution, adding a non-solvent to the solvent, the non-solvent miscible with the silicone and the dexamethasone having a solubility in the non-solvent of below about 5 mg/ml, and curing the solution to form the silicone coating on the electrode carrier.

In some embodiments, the non-solvent may be added to the solvent to form a solvent mixture before dissolving the silicone and the dexamethasone in the solvent to form the solution. In this case, the dexamethasone may be added to the solvent mixture and then the silicone may be added to the solvent mixture. Alternatively, the non-solvent may be added to the solvent after dissolving the silicone and the dexamethasone in the solvent. The non-solvent may be added in an amount of 10% or 5% by volume below a saturation of the dexamethasone in the solution. The total solid concentration may be between about 6% by weight to about 10% by weight in the solution. The concentration of the dexamethasone in the silicone coating may be between about 10% by weight to about 20% by weight of the silicone coating. The solvent may be tetrahydrofurane. The non-solvent may be unsubstituted or substituted aliphatic, cycloaliphatic or aromatic hydrocarbons. For example, the non-solvent may be n-hexane or isomers therefrom, n-pentane or isomers therefrom, cyclopentane, n-heptane or isomers therefrom, n-octane or isomers therefrom, n-nonane or isomers therefrom, n-decane or isomers therefrom, n-dodecane or isomers therefrom, benzene, toluene, and/or xylene. The non-solvent may be n-hexane and the solvent may be tetrahydrofurane. In this case, the ratio of tetrahydrofurane to n-hexane by volume may be about 77/23 in the solution. The dexamethasone solubility in the non-solvent may be below about 1 mg/ml. The method may further include applying the solution to the electrode carrier before curing the solution. The method may further include applying the solution to a substrate before curing the solution, and then transferring the coating from the substrate to the electrode carrier. The method may further include applying the solution to a substrate before curing the solution, and then fixing the substrate with the coating to the electrode carrier. The silicone coating may be applied to, transferred to, or fixed to the electrode carrier in the shape of rings, lines, spots, or combinations thereof between at least two electrode contacts. The solution may be applied using non-contact micro dispensing systems and/or contact dispensing systems. For example, the non-contact micro dispensing systems may be pipe jet dispensing systems, jet-forming dispensing systems, and/or dynamic drop dispensing systems. The curing may include a two-step heat treatment process that includes a first heat treatment between about 50 and 90° C. for about 1 to 3 hours and a second heat treatment at a higher temperature between about 90° C. and 140° C., preferably around 140° C., for about 2 hours. The electrode carrier may be formed from a Liquid Silicone Rubber or Low Consistency Elastomer having a durometer hardness measurement of between about 25 and 50 Shore A. An implantable electrode may be formed according to any of the processes described above.

BRIEF DESCRIPTION OF THE DRAWINGS

The foregoing features of the embodiments will be more readily understood by reference to the following detailed description, taken with reference to the accompanying drawings, in which.

DESCRIPTION OF ILLUSTRATIVE EMBODIMENTS

Various embodiments of the present invention provide a method of forming a silicone coating with an embedded drug, such as dexamethasone, on an electrode carrier for use in a cochlear implant system in order to obtain a desired, controllable release rate of the drug into the perilymph of the cochlea. The coating may be formed directly onto the electrode carrier, may be applied by transferring the coating from a peelable substrate, or may be a part or parts coated with the coating and the coated part(s) are fixated to the electrode carrier. The method produces a thin, uniform coating, e.g., having a thickness of less than about 100 µm, without substantial agglomerates, which may detrimentally burst open during insertion of an electrode and release an uncontrolled amount of dexamethasone in the perilymph. Details of illustrative embodiments are discussed below.

Figure 1:
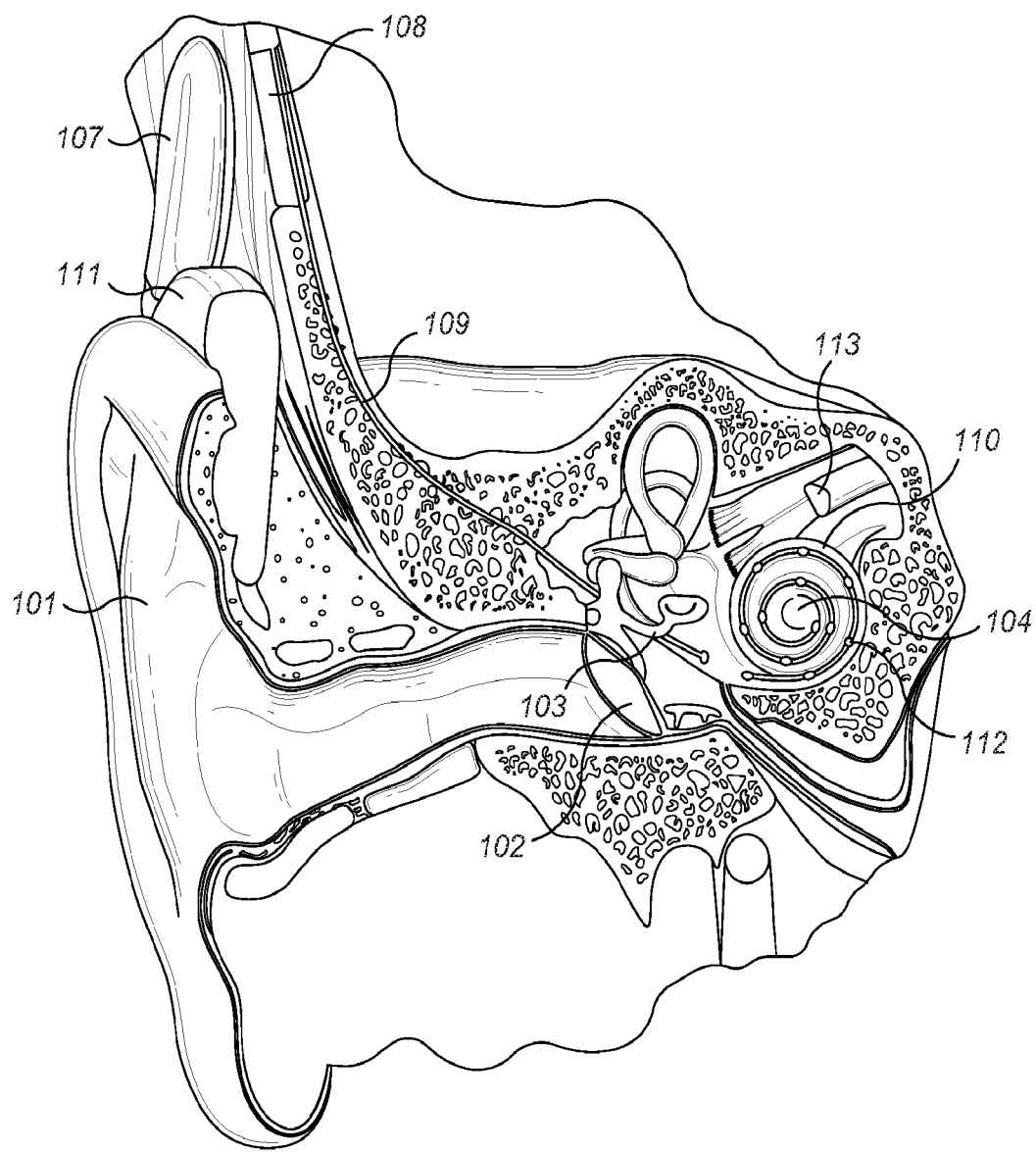
FIG. 1 shows anatomical structures of a human ear having a cochlear implant system.
Figure 2:
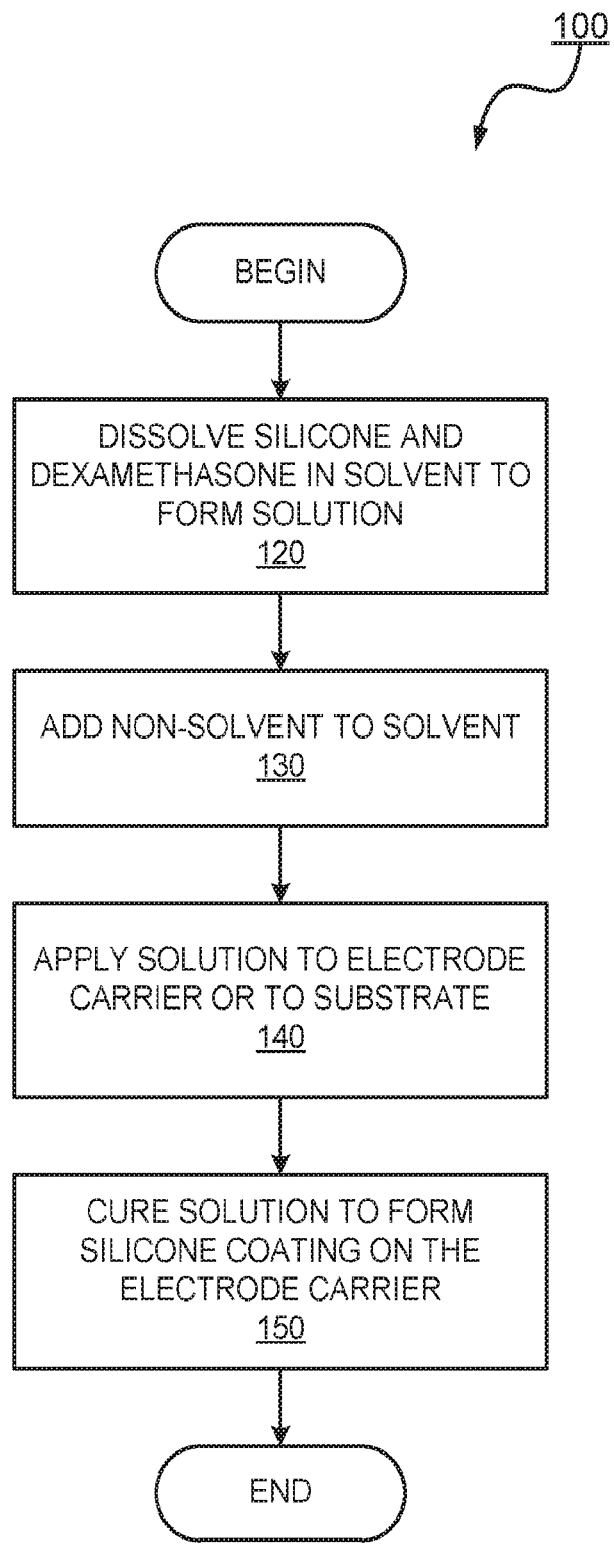
FIG. 2 shows a process of forming a silicone coating on an electrode carrier according to embodiments of the present invention.
Figure 3:
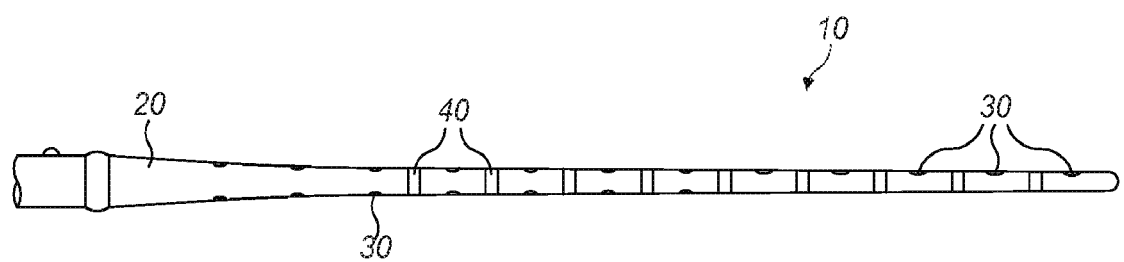
FIG. 3 shows a silicone coating formed on an electrode carrier according to embodiments of the present invention.

FIG. 2 shows a process 100 of forming a silicone coating 40 on an electrode carrier 20 and FIG. 3 shows the silicone coating 40 formed on the electrode carrier 20 by the process according to embodiments of the present invention. The process begins at step 120, in which silicone and dexamethasone are dissolved in an appropriate solvent to form a homogeneous and dispensable solution. The silicone may be a Liquid Silicone Rubber (LSR) or Low Consistency Elastomer, e.g., having a durometer hardness measurement of between about 25 to about 50 Shore A. For example, the silicone may be a two-part addition curing silicone elastomer having a durometer measurement of about 25 to 50 Shore A, having a self-adhesion to the electrode carrier 20 of an electrode 10 and capable of being cured within about 1 hour at 100° C. For instance, the silicone may be formed from commercially available silicone MED-4244 (NuSil Technology LLC, Carpinteria, Calif.) or Liquid Silicone Rubber part no. 40082 (Applied Silicone Corporation, Santa Paula, Calif.) or an equivalent material.

In step 130, a non-solvent is added to the solvent to form a solvent mixture, with the non-solvent being miscible with the silicone and being substantially immiscible with the dexamethasone. For example, the dexamethasone may have a solubility in the non-solvent of below about 5 mg/ml, and preferably below about 1 mg/ml. The solvent may be tetrahydrofurane (THF) and should be volatile. THF has good wettability to the silicone substrate of the electrode carrier 20 and a contact angle on a flat silicone substrate of about 40°. The non-solvent may be an unsubstituted or substituted aliphatic, cycloaliphatic or aromatic hydrocarbon, either branched or straight. For example, the non-solvent may be n-hexane or isomers, n-pentane or isomers therefrom, cyclopentane, n-heptane or isomers, n-octane or isomers, n-nonane or isomers, n-decane or isomers, n-dodecane or isomers therefrom, benzene, toluene, xylene and/or a mixture thereof. For instance, the non-solvent may be n-hexane and the solvent may be THF. In this case, the ratio of THF to n-hexane by volume may be about 77/23 in the solution. The non-solvent may be added to the solvent before dissolving the silicone and the dexamethasone in the solvent. In this case, the dexamethasone may be added to the solvent mixture and then the silicone may be added to the solvent mixture. Alternatively, the non-solvent may be added to the solvent after dissolving the silicone and the dexamethasone in the solvent. The non-solvent may be added in an amount of 10% or 5% by volume below the saturation of the dexamethasone in the solution. Preferably, the solution is kept slightly below the saturation point of dexamethasone. The solution may be kept slightly below the saturation point even without adding the non-solvent in the case that the concentration of dexamethasone in the solvent is less than 10% or about 1 to 10% below the saturation of dexamethasone in the solvent.

In embodiments of the present invention, silicone is used as the drug carrier. The overall viscosity of the solution is mainly from the silicone. The addition of the non-solvent (non-solvent because dexamethasone does not dissolve in it) may result in minor and negligible changes in the viscosity of the solution, but this viscosity change is not believed to be the mechanism that reduces or eliminates the formation of agglomerates. Instead, the low solubility of the dexamethasone in the non-solvent is believed to cause the agglomerates to be substantially reduced or eliminated because the dexamethasone precipitates immediately after the solvent evaporates, which avoids the formation of agglomerates. Preferably, the non-solvent should be added in a ratio close to the saturation of dexamethasone in the final solution in order to reduce or eliminate the formation of the agglomerates. The total solid concentration in the final solution may be in a range of about 6% by weight to about 10% by weight. Preferably, the solvent and non-solvent have a purity of at least 95%.

In step 140, the solution may be applied to an electrode carrier 20 of the electrode 10 or to a substrate. If the solution is applied to a substrate, then the coating may be transferred from the substrate to the electrode carrier or the substrate with the coating may be fixed to the electrode carrier. The electrode carrier 20 has a plurality of contacts 30 disposed on the electrode carrier 20 and may be formed from silicone. The solution may be applied in any shape on the electrode carrier 20. For example, the solution may be applied in the shape of rings, lines, or spots between one or more of the electrode contacts 30 or may be applied in a combination of rings, lines, and/or spots, e.g., a line in the apical region and rings between the contacts 30 in the basal region. As mentioned previously, the contacts 30 may be used to stimulate nerves and/or to record nerve impulses or potentials from the nerves. The electrode 10 may have an electrode lead electrically connecting the electrode 10 to a processor (not shown) for controlling the stimulation and/or recording of the electrode contacts 30. The processor may also provide signal processing capabilities to the stimulation and/or recording signal information. The solution may be applied to the electrode carrier 20 between one or more of the contacts 30 with a commercially available non-contacting micro dispensing system, such as pipe jet, jet-forming or dynamic drop dispensing (ink-jet) systems. Alternatively, the solution may be applied by contact dispensing. The dispensed amount is may be in the range of 1.4 µl/electrode or about 150 nl/ring or spot in the case of 9 rings or spots per electrode. In a further alternative, the solution may be applied to the electrode carrier 20 by means of a peelable substrate, e.g., a polymeric foil, coated with the solution. The solution may be applied to the substrate by any of the above mentioned methods. In addition, the solution may be applied to the substrate by immersing the substrate into the solution. The prepared substrate coated with the solution may be gently pressed against the electrode carrier 20.

In step 150, the solution is cured to form a silicone coating 40 on the substrate or electrode carrier 20 with or without gently pressed substrate thereon. Most of the solvent may be evaporated from the solution at room temperature first and then the silicone coating 40 may be cured in an oven with specific temperature settings. The final coating may have a weight of about 105 µg including 15.75 µg dexamethasone, and a thickness of less than 100 µm, e.g., about 25 µm to about 100 µm. The curing may include a standard heat treatment process for the solution. Optionally, the electrode carrier 20 with solution may be subjected to a two-step heat treatment process to cure the silicone coating 40. In this case, the heat treatment includes a first heat treatment below 90° C. for about 1 to 3 hours and then a second heat treatment at an elevated temperature to help cure the silicone completely. In one embodiment, the temperature of the second heat treatment may be elevated by at least about 5° C., preferably about 10° C. and most preferably about 20° C. For example, the first heat treatment may be between about 50-90° C. for about 1 to 3 hours and the second heat treatment may be between about 90° C. and 140° C., preferably around 140° C., for about 2 hours. For example, the silicone coating 40 may be cured for about 1 to 3 hours at 70° C. with an additional curing step at about 140° C. for 2 hours. With the two-step heat treatment, the release rate of the dexamethasone can be controlled simply with the temperature of curing. A detailed description of a heat treatment process for the silicone coating embedded with dexamethasone may be found in PCT patent application entitled IMPLANTABLE ELECTRODE WITH DEXAMETHASONE COATING, International Appl. No. PCT/US18/17150 filed Feb. 7, 2018, which is incorporated by reference herein in its entirety. After heat curing and when a peelable substrate is pressed onto the electrode carrier 20 in step 130, the substrate may be easily peeled off from the electrode carrier 20 while the coating remains on the electrode carrier 20. The substrate may be peeled off (1) after the first heat treatment and before the second heat treatment, (2) immediately after the second heat treatment or (3) after the second heat treatment and cooling down to a certain temperature, e.g. room temperature. If only the substrate with solution is heat cured, the coated substrate after heat treatment may be gently pressed onto the electrode carrier 20 and, by peeling off the substrate, the coating 40 remains on the electrode carrier 20. For this purpose, use of adhesive may help to transfer the coating 40 from the substrate onto the electrode 10.

The coating 40 is preferably formed from a silicone material because silicone is a material known for releasing embedded drugs, e.g., steroids, is biostable, biocompatible, resistant to sterilization procedures and has the desired properties in terms of elasticity, so that the flexibility of the final, coated electrode 10 is not adversely affected. The silicone coating 40 should have good adhesion to the underlying silicone substrate (i.e., the silicone body of the electrode carrier 20). The coating 40 should also be able to withstand being implanted for a long term. In order to increase the drug release rate, the silicone coating 40 may be loaded with dexamethasone at greater than 10% by weight, e.g., in the range of about 15% by weight to about 20% by weight of dexamethasone in the silicone coating when using an addition curing LSR silicone or Low Consistency Elastomer silicone, e.g., with a durometer of about 40 Shore A. Above 20% by weight, the solution tends to form agglomerates when coated on the electrode carrier 20 even when using embodiments of the present invention.

It is understood that the steps described above may be equally applied to parts that may, after step 150, be fixated to the electrode carrier 20 by means of mechanical fixations or by use of adhesive. Such parts may be formed of various suitable shapes, for example as rings that can be placed over the electrode carrier 20. Using such parts or a substrate to transfer the coating 40 has the advantage that the quality of the coating 40 can be quantified before application to the electrode carrier 20. This significantly reduces the production process risks and avoids unnecessary and expensive rejects of implant devices due to insufficient coating quality.

A coating 40 manufactured according to embodiments of the invention has a surface roughness that is typical for the various production methods (e.g., surface roughness arising from the mold itself) without additional surface roughness caused by the additional dexamethasone in the silicone coating. This is mainly because the liquid solution readily distributes over the surface before becoming final shape during curing. Further, the surface of the silicone with the coating does not show adhesive properties, which is typically the case for silicone (for example, silicone feels slightly sticky or tacky when touched). A thin coating, e.g., of 100 μm thickness, distributed uniformly over the surface with the dexamethasone can only be obtained by dispensing a fluid, for example, a solution according to embodiments of the invention.

As used herein, the term applying a coating to the electrode carrier includes all the above described methods and without limitation includes transfer by a peelable substrate, fixated and coated parts. As used herein, the term "or" used in connection with a list of items, means one or more of the items in the list, but not necessarily all of the items in the list.

EXAMPLES

A set of experiments were conducted to show the feasibility of the coating process embedded with dexamethasone formed according to embodiments of the present invention.

Example 1

In an attempt to reduce the formation of agglomerates, the surface properties of the silicone electrode carrier were modified to reduce the surface energy and improve wettability. The silicone surface was turned more hydrophilic by plasma treatment. A solution of THF, as single solvent, comprising 1.38% by weight dexamethasone and 7.81% by weight silicone was dispensed onto the electrode carrier. A non-solvent was not added to the solution. The contact angle of the solution on the silicone substrate surface was below 10° after plasma treatment. Even with plasma treatment and a high wettability of the solution to the substrate surface, agglomerates still occurred when the solution was dispensed onto the electrode carrier and the silicone coating was cured. Therefore, reducing wettability (e.g., by reducing surface tension or treating the surface of the substrate) to reduce the agglomeration of dexamethasone was not successful when only a solvent was used without a non-solvent.

Example 2

Figure 4A:
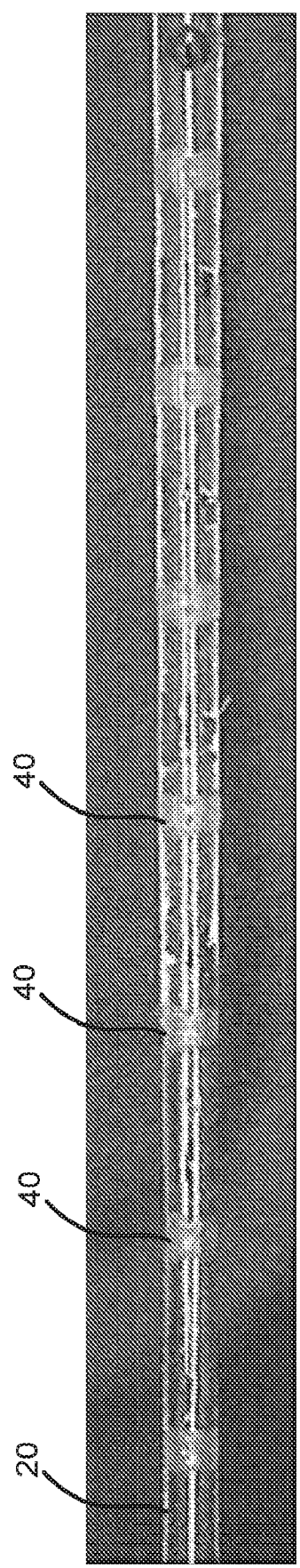
FIG. 4A is a photomicrograph showing silicone coatings on an electrode carrier.
Figures 4B, 4C, 4D, 4E, 4F:
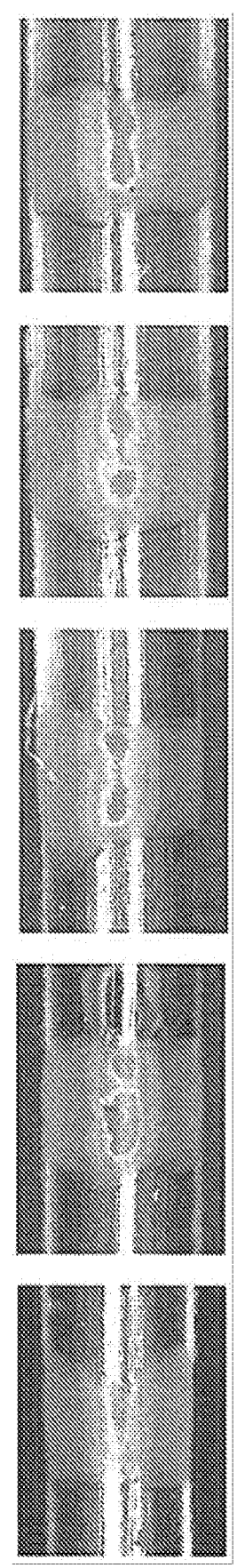
FIGS. 4B-4F are photomicrographs showing close-up views of the silicone coatings shown in FIG. 4A according to embodiments of the present invention.

A solution was prepared by forming a solution of n-hexane and THF at 23% by volume and then adding dexamethasone to get a concentration of 1.38% by weight. Mixed silicone (PART A and PART B) of MED 1-4244 was added in a concentration of 7.81% by weight. The solution was dispensed with a micro dispensing system to give 9 rings between the contact plates with about 105 μg of coating. The solution was cured at 140° C. for 2 hours to form the silicone coating. The experiment was carried out in an environmentally controlled area with a temperature around 23° C. with 48% to 51% humidity. FIG. 4A is a photomicrograph showing the coating on the electrode carrier, and FIGS. 4B-4F show close up views of the coatings. As can be seen, a thin, relatively uniform coating is formed without any agglomerates and the thickness of the coating was less than 100 μm.

Example 3

A solution was prepared by forming a solution of n-hexane and THF at 23% by volume (the ratio of THF/n-hexane was 77/23) and then adding dexamethasone to get a concentration of 1.38% by weight. Mixed silicone (PART A and PART B) of MED 1-4244 was added in a concentration of 7.81% by weight. The solution was dispensed with a micro dispensing system to give 9 rings between the contact plates with about 105 μg of coating. The experiment was carried out in an environmentally controlled area with a temperature around 23° C. with 48% to 51% humidity. Three coated electrodes were then subjected to each of the following heat treatment parameters:

Heat Treatment A—3 electrodes for 3 hours at 70° C. and 2 hours at 140° C.;

Heat Treatment B—3 electrodes for 1 hour at 70° C. and 2 hours at 140° C.; and

Heat Treatment C—3 electrodes for 2 hours at 140° C.

Figure 5:
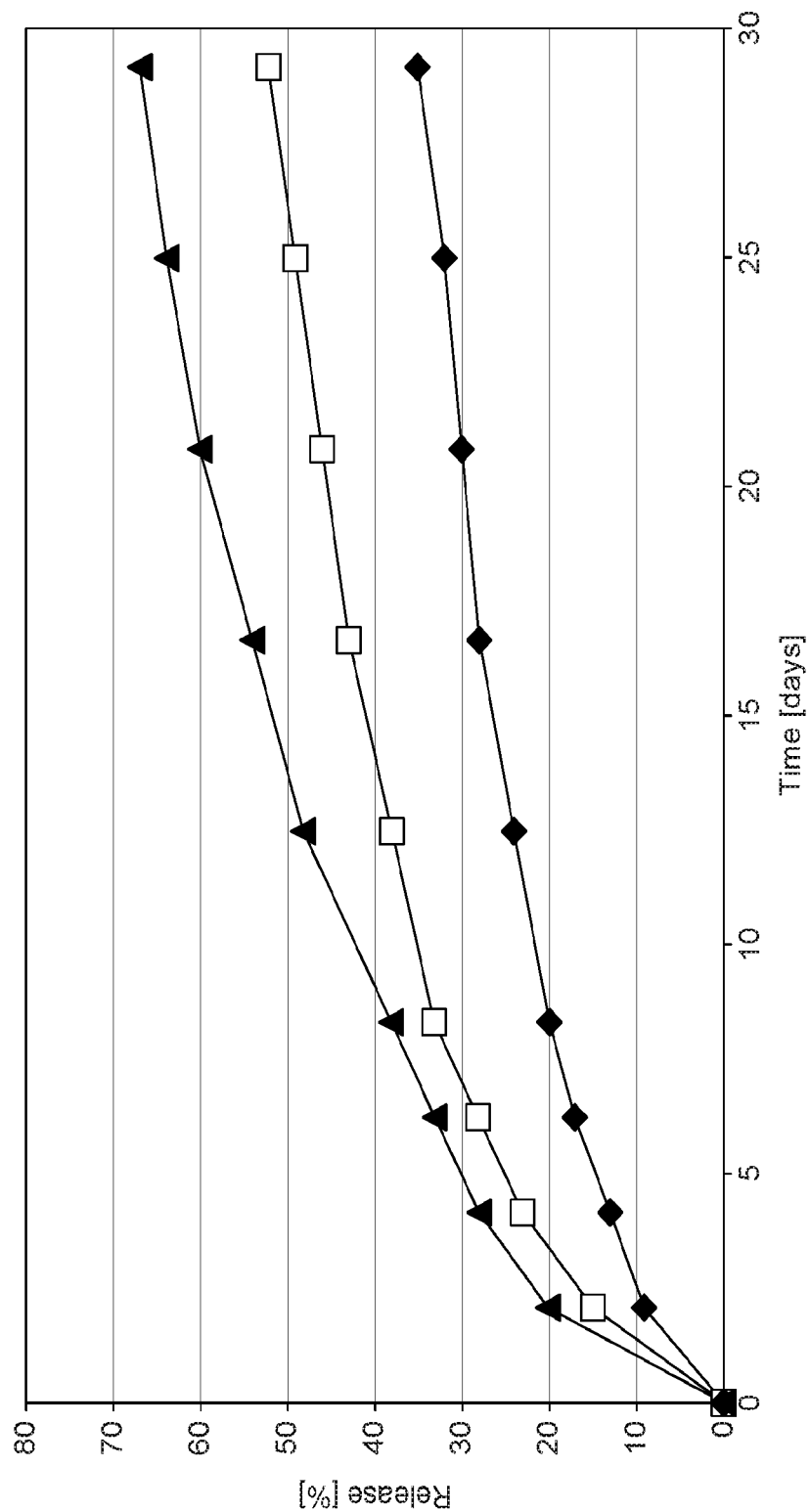
FIG. 5 is a graph showing the release rate as a function of time for three heat treatment processes according to embodiments of the present invention.

A graph of the release rate of the drug as a function of time is shown in FIG. 5 for the three sets of heat treatment parameters. Heat Treatment A is the upper curve (triangles), Heat Treatment B is the middle curve (squares), and Heat Treatment C is the bottom curve (diamonds). Therefore, the release rates of the silicone coatings embedded with the dexamethasone may be further tailored based on the subsequent heat treatment parameters used.

Although the above discussion discloses various exemplary embodiments, those skilled in the art may make various modifications to, or variations of, the illustrated embodiments without departing from the inventive concepts disclosed herein.

What is claimed is:

1. A method of forming a silicone coating on an electrode carrier for use in cochlear implant systems, the method comprising:

dissolving silicone and dexamethasone in a solvent to form a solution;

adding a non-solvent to the solvent, the non-solvent miscible with the silicone, the dexamethasone having a solubility in the non-solvent of below about 5 mg/ml; and curing the solution to form the silicone coating on the electrode carrier.

2. The method of claim 1, wherein the non-solvent is added to the solvent to form a solvent mixture before dissolving the silicone and the dexamethasone in the solvent to form the solution.

3. The method of claim 2, wherein the dexamethasone is added to the solvent mixture and then the silicone is added to the solvent mixture.

4. The method of claim 1, wherein the non-solvent is added to the solvent after dissolving the silicone and the dexamethasone in the solvent.

5. The method of claim 1, wherein the non-solvent is added in an amount of 10% by volume below a saturation of the dexamethasone in the solution.

6. The method of claim 1, wherein the non-solvent is added in an amount of 5% by volume below a saturation of the dexamethasone in the solution.

7. The method of claim 1, wherein total solid concentration is between about 6% by weight to about 10% by weight in the solution.

8. The method of claim 1, wherein concentration of the dexamethasone in the coating is between about 10% by weight to about 20% by weight of the coating.

9. The method of claim 1, wherein the solvent includes tetrahydrofurane.

10. The method of claim 1, wherein the non-solvent includes unsubstituted or substituted aliphatic, cycloaliphatic or aromatic hydrocarbons.

11. The method of claim 10, wherein the non-solvent includes n-hexane or isomers therefrom, n-pentane or isomers therefrom, cyclopentane, n-heptane or isomers therefrom, n-octane or isomers therefrom, n-nonane or isomers therefrom, n-decane or isomers therefrom, n-dodecane or isomers therefrom, benzene, toluene, xylene or combinations thereof.

12. The method of claim 1, wherein the non-solvent is n-hexane and the solvent is tetrahydrofurane, and the ratio of tetrahydrofurane to n-hexane by volume is about 77/23 in the solution.

13. The method of claim 1, wherein the dexamethasone solubility in the non-solvent is below about 1 mg/ml.

14. The method of claim 1, further comprising applying the solution to the electrode carrier before curing the solution.

15. The method of claim 14, wherein the coating is applied to the electrode carrier in the shape of rings, lines, spots, or combinations thereof between at least two electrode contacts.

16. The method of claim 14, wherein the solution is applied using non-contact micro dispensing systems or contact dispensing systems.

17. The method of claim 16, wherein the non-contact micro dispensing systems include pipe jet dispensing systems, jet-forming dispensing systems, dynamic drop dispensing systems, or combinations thereof.

18. The method of claim 1, further comprising applying the solution to a substrate before curing the solution, and then transferring the coating from the substrate to the electrode carrier.

19. The method of claim 1, further comprising applying the solution to a substrate before curing the solution, and then fixing the substrate with the coating to the electrode carrier.

20. The method of claim 1, wherein the curing includes a two-step heat treatment process that includes a first heat treatment between about 50 and 90° C. for about 1 to 3 hours and a second heat treatment at a higher temperature between about 90° C. and 140° C. for about 2 hours.

21. An implantable electrode formed according to the method of of claim 1.

* * * * *